United States Patent [19]
Akamatsu et al.

[11] Patent Number: 5,910,412
[45] Date of Patent: Jun. 8, 1999

[54] METHOD FOR IDENTIFYING THE SEX OF SPINACH BY DNA MARKERS

[75] Inventors: Toyokazu Akamatsu, Kimitsu; Takao Suzuki, Sodegaura, both of Japan

[73] Assignee: Sakata Seed Corporation, Yokohama, Japan

[21] Appl. No.: 08/855,449

[22] Filed: May 13, 1997

[30] Foreign Application Priority Data

May 14, 1996 [JP] Japan .................................... 8-119124

[51] Int. Cl.$^6$ .............................. C12Q 1/68; C12Q 1/04; C07H 21/04
[52] U.S. Cl. .................................. 435/6; 435/29; 435/34; 536/23.1; 536/23.6; 536/24.1
[58] Field of Search .............................. 435/4, 6, 29, 34, 435/320.1, 41, 410; 536/23.1, 24.1, 23.6

[56] References Cited

PUBLICATIONS

Chen et al. A Chloroplast DNA Deletion Located in RNA Polymerase Gene rpoC2 in CMS Lines of Sorghum. Mol. Gen. Genet. 236: 251–259, 1993.
J.R. Ellis, et al., American Journal of Botany, vol. 47, pp. 210–214, "The Chromosomes of *Spinicia Oleracea*", Mar. 1960.
Muneo Iizuka, et al., Genetics, vol. 47, pp. 1225–1241, 1962, "Cytogenetic Analysis of Sex Determination in *Spinacia Oleracea*".
Shintaro Sugiyama, et al., Bulletin of the National Institute of Agricultural Sciences, Series D, No. 11, pp. 211–236, 239, 272, 275–329, "Studies on the Artificial Control of Sex Expression in Spinach", Mar. 1964 (with partial English translation).
John G. Williams, et al., Nucleic Acids Research, vol. 18, No. 22, pp. 6531–6535, 1990, "DNA Polymorphisms Amplified by Arbitrary Primers are Useful as Genetic Markers".
I. Paran, et al., Theor. Appl. Genet., vol. 85, 985–993, 1993, "Development of Reliable PCR–Based Markers Linked to Downy Mildew Resistance Genes in Lettuce".
D.L. Mulcahy, et al., Sex Plant Reproduction, vol. 5, pp. 86–88, 1992, "DNA Probes for the Y–Chromosome of Silene Latifolia, A Dioecious Angiosperm".
F.M. Restivo, et al., Theor. Appl. Genet., vol. 90, pp. 124–128, 1995, "Linkage Arrangement of RFLP LOCI in Progenies From Crosses Between Doubled Haploid Asparagus Officinalis L. Clones".
Koichi Sakamoto, et al., Plant Cell Physiol., vol. 36, No. 8, pp. 1549–1554, 1995, "A Male–Associated DNA Sequence in a Dioecious Plant, *Cannabis Sativa* L.".
Charles Ainsworth, et al., The Plant Cell, vol. 7, pp. 1583–1598, Oct. 1995, "Male and Female Flowers of the Dioecious Plant Sorrell Show Different Patterns of Mads Box Gene Expression".
Hormaza J et al: "Identification of a RAPD marker linked to sex determination in Pistacia vera using bulked segregated analysis", Theor. Appl. Genet, vol. 89, 1994, pp. 9–13, XP002050702, *full document*.
Lionakis S.: "Genetics and physiology of sex determination in dioecious plants", Fruits, vol. 40, No. 11, 1985, pp. 739–743, XP002050703, *full document*.
Database WPI, Week 8117, Derwent Publications Ltd., London, GB; An 810–d8045d, XP002050728, "Establishing the sex of plants" & SU 755 248 B *IIRZHI P), Aug. 18, 1980, *summary*.
Al–Khayri J et al: "In vitro seed production from sex–modified male spinach plants regenerated from callus cultures" Scientia Horticulturae, vol. 52, 1992, pp. 277–282, XP002050704.

*Primary Examiner*—Nancy Degen
*Attorney, Agent, or Firm*—Oblon, Spivak, McClelland, Maier & Neustadt, P.C.

[57] ABSTRACT

The invention relates to a method for identifying the sex of spinach wherein a DNA specifically present in a male plant of spinach is used as the marker as well as to a DNA used therefor. The object of the invention is to provide a method for easily and rapidly identifying the sex of spinach

24 Claims, 8 Drawing Sheets

T11A (T7 SIDE)

```
TTCCCCGCGA CTTCACACTC GTCATTTCAT TCTCGACCCT AATTAACTCC TCTTTACCCA   60
   OPT11        1-7 primer              TAF1-7 primer
ATTAGAAATC AATGCTGAAA AAAGTCTATT TCGAAATCTA GCCCTTTGTT TTTAGTCATG  120

TTTTTTGTCT AATCTATGTA AAAATCTAGG TTAAACATAA TATATTTCCA ATTTGTTATG  180

GAAGGAAGAC TTATATATAT GCTTATATTG TGGGGATTCT ATGAGAATCA GTTCAACCAC  240

TACATCAGAT TGATTTGTTT ATGCATTTTG TCCAAATATC ATGTTATCAT ATACTTGTAT  300

TTAATTTCTC GAACATATTA TTAAGCCTAG GACTGTTATG ATAATGGGGC TTGTATTTCT  360
              INT1-7 primer            COMT primer
TATGGGAGGG GAAATGCATC ATTGATTTCC AATGAAATGG GAATTAGTT             409
```

FIG. 8

V20A (T3 SIDE)

```
TTCCCCGCGA TAGAGTGTCA AACCACAAGC AAACAATGAA TTCAAATTAC CAATAAAAAA   60
   OPT11          1-3 primer
TTCATACGAG AAAGCTACGA GATCACAACC AAGAAGTCTG CAATTCTGCA AAAAAAAACG  120
     TAF1-3 primer
TGAACATACA CTACTTTTAA AGAGATTAAC TGGATGAGAA CACTTACATA AGTAATATCC  180

CTACAGCCCC CTTCATTCTA CAGCAGAAAT CTTTGCATCA CAAGCTATAA TCCCAAAAAT  240

ACACATACCA GATATGACCA ACACTAACAA AAAAATAGAA AACATAAGTA CACATGCCAG  300
                                                      INT1-3 primer
GAAGCTGAAA CGTAGAAATA GACTCACAAA                                   330
    COPT primer
```

FIG. 9

V20A (T7 SIDE)

```
     CAGCATGGTC CCTACCGTTG AATCAGTTGT TGTAAGGTAA AGCCTGAGTG GAGAACCCGA    60
     ‾‾‾‾‾‾‾‾‾‾ ‾‾‾‾‾‾‾‾‾‾‾‾‾‾‾‾‾‾‾‾‾‾‾‾‾‾‾‾‾‾‾‾‾→
        OPV20           101-7 primer
     TATTGTTGGC TTTAACACTG GTGGATTTGA AAATTAGTCC TTGATGGTGT CAAATGCGTA   120

TTGGCAGCCT TCGTCCCATA CCTTGGGCTC ACTCTTGTGG AGTTTTTGGA ACACTTCTC    180

ACAAATCATG GTGAGTTTTA AAATGTACCT GTTGATGTAT TGTAACTTGC CAAGGAACTC   240

CCAAATTTCG TTCTCATTTG CCGGCGATTT CATGTCTAGA CTGGCCTTGT TTTTTGAAGG   300

ATCAGCCTCG ATGCCCTGAG AACTGATGAC ATACCCGAGT AACTTGCCTG ACGTGACCCT   360
                                                              ‾‾‾‾‾‾‾‾‾
     GAATGCACAT TTCTGAGGAT TGAGCCTCAT ATTGTATTGT CTGAGCTTGT AGAAGAATTT   420
     ‾‾‾‾‾‾‾‾‾‾‾‾‾‾‾‾‾‾‾‾→  ←‾‾‾‾‾‾‾‾‾‾‾‾‾‾‾‾‾‾‾
       IN101-7 primer           CDMV primer
     TCGAAGTACT                                                         430
```

FIG. 10

V20A (T3 SIDE)

```
     CAGCATGGTC CTATCATGAT ATGCCAGGGG TTGATCCAAG CATCGGTTAA CATACAATTC    60
     ‾‾‾‾‾‾‾‾‾‾             ‾‾‾‾‾‾‾‾‾‾‾‾‾‾‾‾‾‾‾‾‾‾‾‾‾‾‾‾‾‾‾‾‾‾‾‾‾‾‾‾→
        OPV20                          101-3 primer
     CCCTCATTTC AGGCATAAAT CCCATCAAGA AAAAACTCCG TCGTGTGAAA CCGGGTGTTT   120

CCCTCAAAAT TAAAGAAGAG GTCTCCAAGC AGTTAGAGGT CGGGTTTATT CGAGAATCCA   180

AATATTCAGA ATTGATTGCA AATGTCGTTC CAGTTCCGAA GAAGGACGGT AAATTTCAAA   240

TGTGCGTCGA TTACAGATAT CTTAACACGA CTAGCCCTAA AGACGATTTT CCACTGCCAC   300

TCATCGACAT TCTGGTCGAC AACACAGCCA ATTATGCCTT ACTCTCTTTT ATGAACTGGT   360
                                      ‾‾‾‾‾‾‾‾‾‾‾‾‾‾‾‾‾‾‾‾→  ←‾‾‾‾‾‾‾‾‾
                      IN101-3 primer                         COPV primer
     ACGCAGGCTA CAATCGGATT CCCA                                         384
```

FIG. 11

V20C (T3 SIDE)

```
   CAGCATGGTC AACTTTGGAA CAAAACACAC GAAGTCAACA TTTCAGGTTA TAAAGGAATT    60
   ‾‾‾‾‾‾‾‾‾‾ ‾‾‾‾‾‾‾‾‾‾‾‾‾‾‾‾‾‾‾‾‾‾‾‾‾‾‾‾‾‾‾‾→
      DPV20            12-7 primer
   CCTAAGGCAC ACAGGCCAAA TTGCACAAAA GCACCATCAA TGCATGTGCA GCAGCTGCAT   120

CAAAGANTAG CAAATNATGC AGACGGTACC AGTAGTTCAT ATGCAGCAGC TGCACCAAGC   180

AGTCAAGAAC GTCAATGCAC CAGCAGCAGC AGNACAANGC ATCANGTATA AAGCANTANC   240

TTCATAAGAA CTGCATAACA TACACTAGAN CAAACANCAA GCCTGTATAA NGGGCTATAG   300

TCAGCAGGCT CCCAGCAAGC CTGATCAGNA GGTTNCTNGC AAGNCTGCTT TTGAGTAAGG   360

TTCAA                                                               365
```

*FIG. 12*

V20C (T7 SIDE)

```
   CAGCATGGTC TTGCATTGTG CATGATAACG GAGTAATACA GTTATTGACT TGCCTCTCAT    60
   ‾‾‾‾‾‾‾‾‾‾ ‾‾‾‾‾‾‾‾‾‾‾‾‾‾‾‾‾‾‾‾‾‾‾‾‾‾‾‾‾‾‾‾→
      DPV20            12-3 primer
   TGACATCATA TATAGTATAA ATGGAAAACA TTGACATCAA CAAACCCCAA ACCTTAGTAC   120

TGGTTGTATA TAAACTGGTG TTGTTGTTGT CCTTGTATCA CANCTCGGCT CTATAGGTGT   180

CGAACCTGGG CCTAGACCCT CGGAATGGAA GGTCTATTAA GAAAAGTTAG ATGCCTAGTT   240

CATGCATTAG TAAATCTACT TCTGCATTCA GCATTTGANT TATACTGGCC ATTGTGCATT   300

CGGTCAACCG GCCAATGGCT TTACCAACCC ANGCCCCTGC CTGT                    344
```

*FIG. 13*

METHOD FOR IDENTIFYING THE SEX OF SPINACH BY DNA MARKERS

FIELD OF THE INVENTION

The present invention relates to a method for easily and rapidly identifying the sex of spinach before bolting and DNAs used therefor.

BACKGROUND OF THE INVENTION

Spinach is a dioecious plant where a male plant with male flowers, a female plant with female flowers and an intermediate plant with both male and female flowers are present. It is estimated that the mode of inheritance has a similar mechanism to XY type generally seen in animals and the sex determining genes are located on chromosome 1 as multiple alleles (Ellis and Janick 1960, Am. J. Botany 47, 210–214; Iizuka and Janick 1962, Genetics 47, 1225–1241; Sugiyama and Suto, Bull. Nat. Inst. Agr. Sci. (Japan) Series D, No. 11, 211–329 (1964)).

For such dioecious plants, it is important to identify the sex of individuals obtained by screening in a breeding process rapidly in order to improve the efficiency of breeding operations. However, the male and female of spinach cannot be definitely judged until the morphological differences between the male and female clearly appear after bolting, because the difference in karyotype between male and female spinach is not so clear as in the animal to make the discrimination of the sex chromosome difficult.

Conventional methods for early identifying the sex of plants include those using DNA markers such as RAPD (Random Amplified Polymorphic DNA) marker, SCAR (Sequence Characterized Amplified Regions) marker, etc. The RAPD method which is a technique based on the PCR method, was developed by Williams (Nucleic Acids Res 18, 6531–6535 (1990)), and for its relatively easy procedures, this method became rapidly widespread for plants as the main object. However, unexpected experimental errors can occur depending on DNA purity, PCR unit, etc., since the annealing temperature (35 to 42° C. ) in the RAPD method is set lower than in the conventional PCR method. On the other hand, the SCAR method was developed by Paran and Michelmore (Theor Appl Genet 85:985–993 (1993)) in which a region with less experimental errors is amplified using PCR primers synthesized on the basis of a nucleotide sequence of a RAPD marker.

Although these DNA markers are extremely useful means for identifying the sex of plants, there are very few cases ever reported including White Campion (*Melandrium album* Garcke) and Pistachio(*Pist acia vera* L.) (Mulcahy et al., Sex Plant Reprod, 5, 86–88 (1992); and Hormaza et al., Theor Appl Genet, 89, 9–19 (1994)), and there is none of such reports on spinach.

SUMMARY OF THE INVENTION

As described above, the means of identifying the sex of spinach before bolting has still not been established, and this is a factor of low efficiency of spinach breeding and seed production. The present invention was made to solve this problem, and the object of the present invention is to provide a means for easily and rapidly identifying the sex of spinach at the stage of seedlings.

As a result of eager research by the present inventors, they found DNAs exist specifically in male plants of spinach to complete the present invention.

That is, the present invention relates to a method for identifying the sex of spinach, wherein DNAs specifically exist in male plants of spinach are used as markers.

The sex of spinach can be identified easily and rapidly before bolting by the method of the present invention.

BRIEF DESCRIPTION OF THE DRAWINGS

FIG. 8 shows the positional relationship between the T7 side nucleotide sequence of T11 A and primers for its amplification.

FIG. 9 shows the positional relationship between the T3 side nucleotide sequence of T11 A and primers for its amplification.

FIG. 10 shows the positional relationship between the T7 side nucleotide sequence of V20 A and primers for its amplification.

FIG. 11 shows the positional relationship between the T3 side nucleotide sequence of V20 A and primers for its amplification.

FIG. 12 shows the positional relationship between the T7 side nucleotide sequence of V20 C and a primer for its amplification.

FIG. 13 shows the positional relationship between the T3 side nucleotide sequence of V20 C and a primer for its amplification.

DETAILED DESCRIPTION OF THE INVENTION

Figure 1:
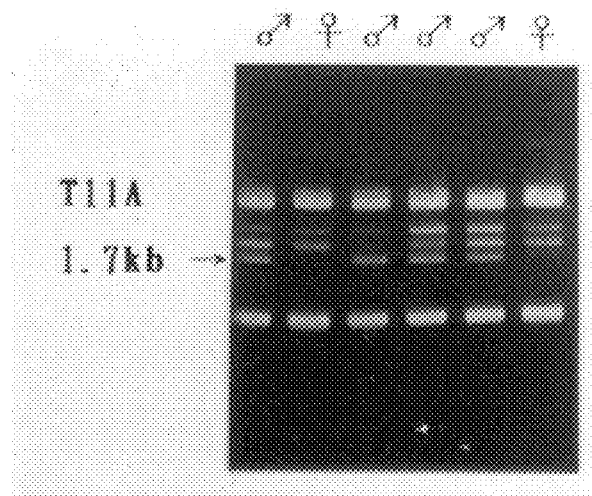
FIG. 1 is a photograph of a profile in electrophoresis of RAPD products with DNA extracted as a template from Atlas sib-cross progeny (primer: OPT11).

Hereinafter, the present invention is described in detail.

The method for identifying the sex of spinach according to the present invention is effected using DNAs specifically exist in male plants of spinach as markers.

The method for identifying the sex of spinach according to the present invention can be applied to any variety insofar as it is a plant belonging to spinach i.e. *Spinacia oleracea* L.

The DNA used as the marker (hereinafter referred to as "marker DNA") is not particularly limited insofar as it exists specifically in male plants of spinach, and it includes e.g. T11A, V20A, V20C, or a DNA identical with a part thereof. "T11A" is a DNA which is shown in SEQ ID No.1. "V20A" is a DNA which is shown in SEQ ID No.2. "V20C" is a 0.9 kb long DNA containing the nucleotide sequences of SEQ ID Nos.3 and 4.

Identifying the sex of plants with the marker DNA means to identify male and female plants by some way detecting the characteristic DNAs exist peculiarly in the male plants. Specifically, the means of detecting the marker DNA for includes, but is not limited to, polymerase chain reaction (PCR), Southern blotting etc.

In case PCR is used for detection of the marker DNA, a DNA extracted from spinach to be identified the sex is used as a template and specific DNAs are used as primers in PCR to amplify the region intervening between the primers, and the spinach is identified the sex by examining the amplification product for the presence of the marker DNA. Examples of usable primers are two DNAs identical with a part of e.g. T11A, V20A or V20. Specifically, such primers are "1-7" represented by SEQ ID No.5, "TAF1-7" represented by SEQ ID No.6, "COMT" represented by SEQ ID No.7, "INT1-7" represented by SEQ ID No.8, "1-3" represented by SEQ ID No.9, "TAF1-3" represented by SEQ ID No.10, "COPT" represented by SEQ ID No.11, "INT1-3" represented by SEQ ID No.12, "101-7" represented by SEQ ID No.13, "IN101-7 " represented by SEQ ID No.14, "COMV" represented by SEQ ID No.15, "101-3" represented by SEQ ID No.16, "IN101-3" represented by SEQ ID No.17, "COPV" represented by SEQ ID No.18, "12-7" represented by SEQ ID No.19, and "12-3" represented by SEQ ID No.20. Although an arbitrary combination of 2 primers can be used, preferable combinations are 1-3 and TAF1-7, 1-7 and COMT, 1-7 and TAF1-3, 1-7 and INT1-3, TAF1-3 and TAF1-7, TAF1-7 and COMT, TAF1-7 and INT1-3, 101-7 and IN101-3, and IN101-7 and IN101-3. Among these, the combination TAF1-7 and COMT is particularly preferable. As primers, it is also possible to make use of "OPT11" represented by SEQ ID No.21, "OPQ20" represented by SEQ ID No.22, "OPU16" represented by SEQ ID No.23, and "OPV20" represented by SEQ ID No.24, all of which are used in the RAPD method. The above primers can be related to T11A, V20A and V20C, as shown in FIGS. 8 to 13.

To extract DNA from a plant to be identified the sex, a conventional method can be used without using any special method. Any part of the plant, such as leaves, stems, roots, seeds, embryos, and cultured cells, can be used as DNA sources. PCR can be carried out using conventional temperature and cycles, but if OPT11 , OPQ20, OPU16 or OPV20 is used as the primer, the annealing temperature is preferably set lower than usual.

Because the length of marker DNA can be estimated from the positions of PCR primers in T11A, V20A or V20C, it can be judged by electrophoresis whether the marker DNA is contained in the amplification product.

The preparation of the DNA used in the present invention is as follows: T11A, V20A and V20C, can be prepared from a male of spinach through their selective amplification by PCR using the above-mentioned primers and a male-derived DNA as the template, followed by electrophoresis of the amplification product and their extraction from their corresponding bands from the gel. The primers 1-7, TAF1-7, COMT, INT1-7, 1-3, TAF1-3, COPT, INT1-3, 101-7, IN101-7, COMV, 101-3, IN101-3, COPV, 12-7 and 12-3 are short DNA fragments each consisting of 19 to 25 nucleotides, so they can be synthesized in a commercial DNA synthesizer etc.

EXAMPLES

The present invention is described in more detail by reference to the following examples which are not intended to limit the scope of the present invention.

Example 1

In this example, DNA markers specifically present in male plants of spinach were identified by the RAPD method where DNAs derived respectively from male and female plants of spinach were analyzed.

RAPD markers specifically present in a male plant of spinach were screened in the following manner from progeny (143 individuals) from sib-cross (female×male) of Atlas (F1 variety available from Sakata Seed Corp., Japan). To confirm that the identified RAPD markers can be applied to other strains of spinach, 5 male plants and 5 female plants from each of Eastern 3 strains (Ujou-2, Ujou-3, SPT) and Western 3 strains (ATF, PAF, SDM) were examined in a similar manner.

A 10-mer random primer kit (26 sets (OPA–OPZ) of 20primers) commercially available from Operon Co., was used as primer in RAPD. Twenty to thirty days after seeding, DNA was extracted from each spinach by the PEX method (Jhingan 1992, Methods in Molecular and Cellular Biology 3:15–22). PCR in the RAPD method consisted of 40 cycles where each cycle was carried out at 94° C. (1 minute), 42° C. (1 minute), and 72° C. (2 minutes) using Programmable Control System PC-700 available from Astech. Then, the amplification products were electrophoresed on 1.8% agarose gels, stained with ethidium bromide, and exposed to UV light to visualize bands.

Figure 2:
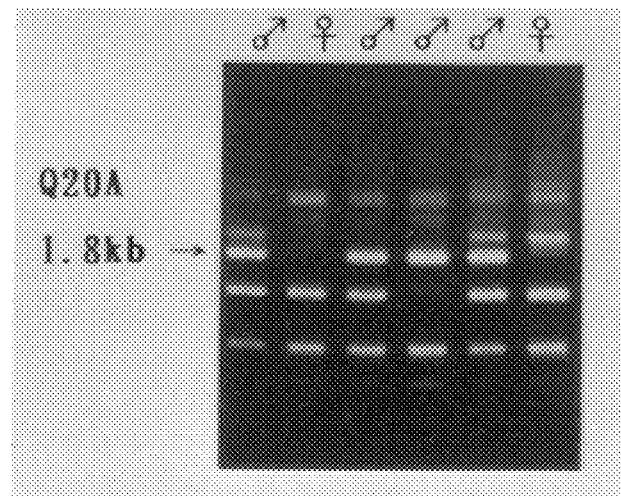
FIG. 2 is a photograph of a profile in electrophoresis of RAPD products with DNA extracted as a template from Atlas sib-cross progeny (primer: OPQ20).
Figure 3:
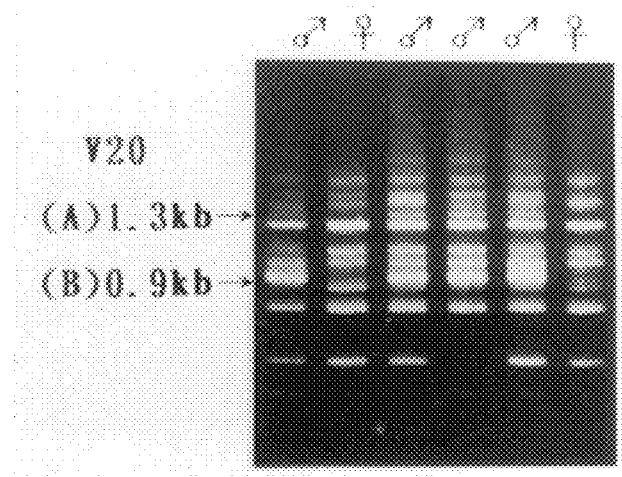
FIG. 3 is a photograph of a profile in electrophoresis of RAPD products with DNA extracted as a template from Atlas sib-cross progeny (primer: OPV20).
Figure 4:
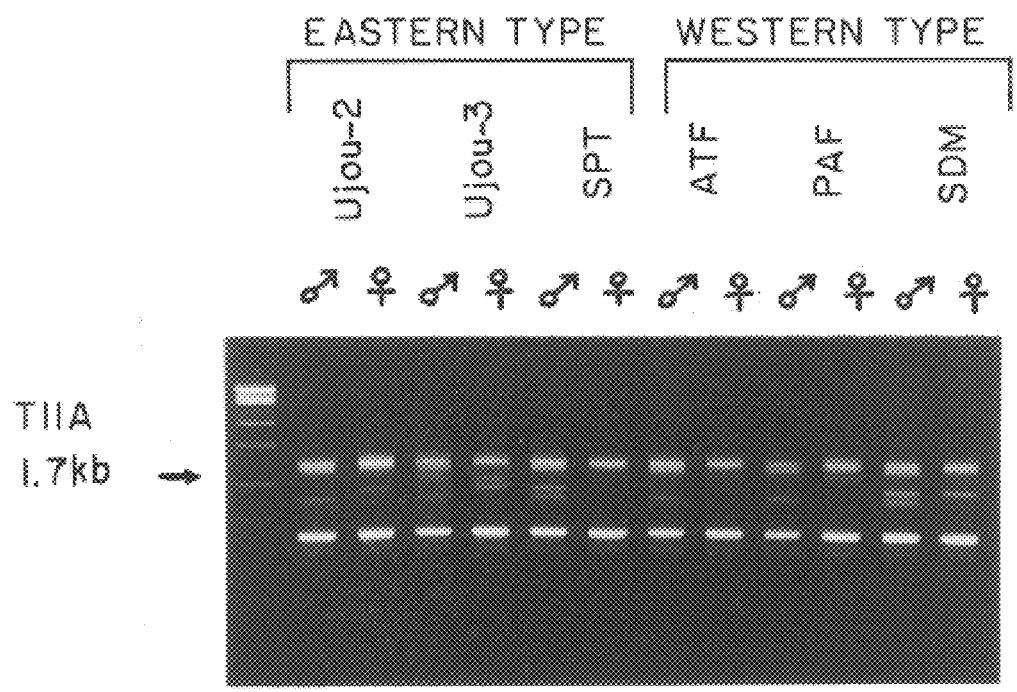
FIG. 4 is a photograph of a profile in electrophoresis of RAPD products from male and female individuals of 3 strains each of Eastern and Western spinach (primer: OPT11).
Figure 5:
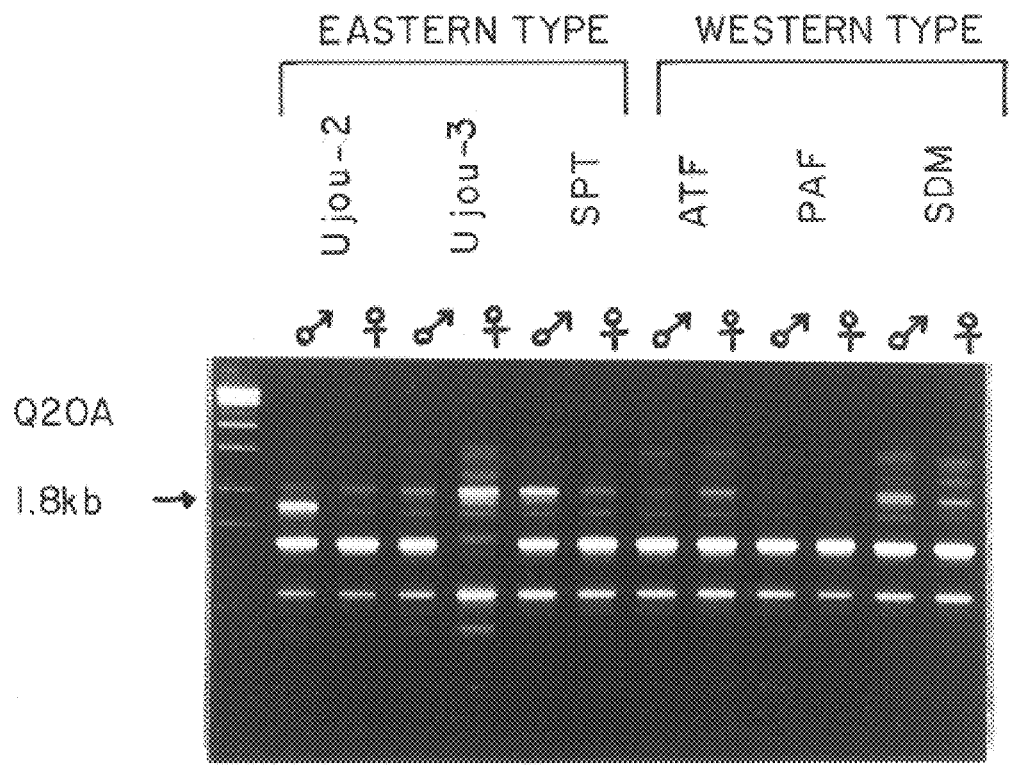
FIG. 5 is a photograph of a profile in electrophoresis of RAPD products from male and female individuals of 3 strains each of Eastern and Western spinach (primer: OPQ20).
Figure 6:
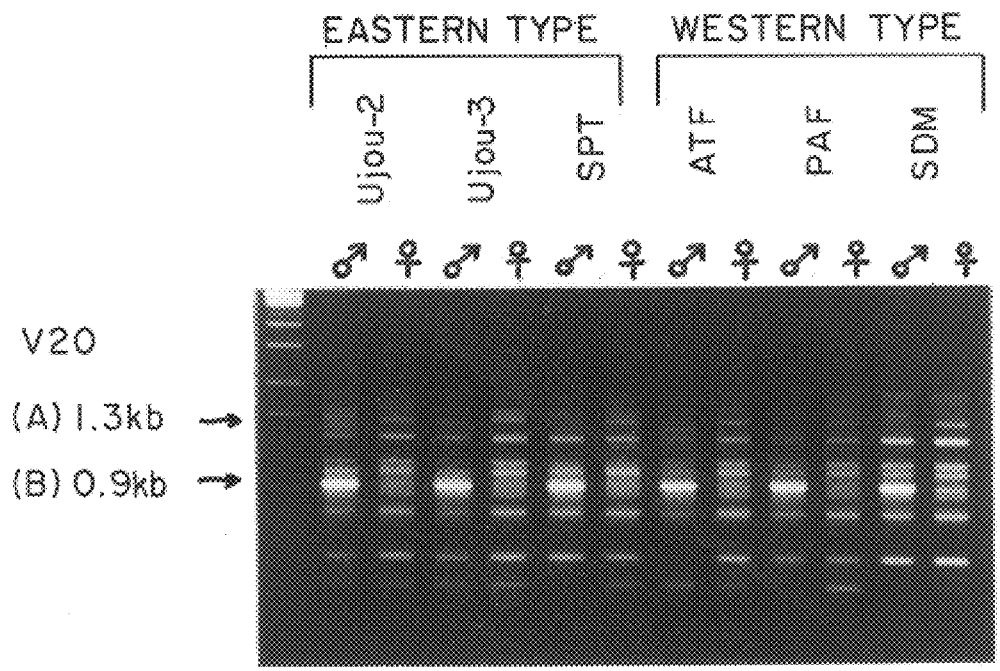
FIG. 6 is a photograph of a profile in electrophoresis of RAPD products from male and female individuals of 3 strains each of Eastern and Western spinach (primer: OPV20).

Five marker bands (T11A, Q20A, U16A, V20A and V20C) specifically present in 100% males in the Atlas sib-cross progeny (143 individuals) were found (FIGS. 1, 2 and 3). As other strains, 3 Western strains and 3 Eastern strains were examined for the presence of the same markers. The results indicated that the marker bands Q20A and U16A were present specifically in the males of some Eastern strains, and that the marker bands T11A, V20A and V20C were present specifically in the male plants of both the Eastern and Western strains (FIGS. 4, 5 and 6). Further examination of their recombination frequency in Atlas sib-cross progeny (667 individuals) indicated that T11A, V20A and V20C recombination frequencies were 0/667 respectively, and Q20A recombination frequency was 1/667. This result indicated that the marker bands T11A (1.7 kb), V20A (1.3 kb) and V20C (0.9 kb) were DNA markers tightly linked to the male-determining gene.

Example 2

Figures 7A, 7B, 7C, 7D:
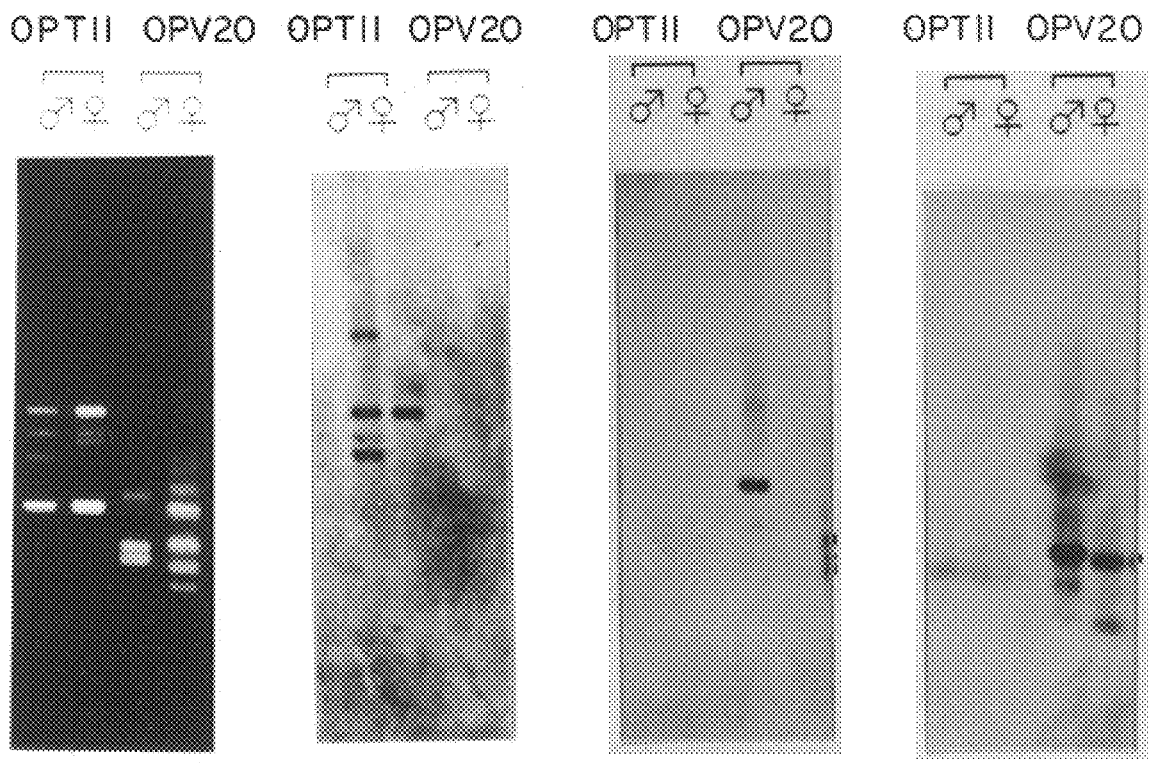
FIG. 7 is a photograph of a profile in electrophoresis of RAPD products.

Each of T11A (1.7 kb), V20A (1.3 kb) and V20C (0.9 kb) was extracted from the gel, then purified, ligated into a SmaI site of a vector (pBluescript SK(–), Toyobo Co., Ltd.), and introduced into *E. coli* (JM109, Toyobo Co., Ltd.) for cloning. To confirm that the respective clones thus obtained correspond to the specific marker bands obtained by the RAPD method, each clone was labeled with digoxigenin and analyzed by Southern hybridization (using a DIG kit, Boehringer Mannheim Co.). The results are shown in FIG. 7. In FIG. 7, "A" shows a profile in electrophoresis of the amplification products when OPT11 and OPV20 were used as primers, and "B", "C", and "D" show profiles in Southern blotting with T11A, V20A and V20C as probes. As shown in FIG. 7, the respective clones were hybridized with the corresponding RAPD products, indicating that the object markers were cloned.

All regions of T11A and V20A, and 300 to 400 bp regions from both terminals of V20C were sequenced in Autosequencer 373A manufactured by ABI Co.

All nucleotide sequence of T11A is shown in SEQ ID No.1; all nucleotide sequence of V20A is shown in SEQ ID No.2; and terminal nucleotide sequences of V20C (0.9 kb) from the T7 side (the side of T7 promoter located in the inserted vector) and T3 side (the side of T3 promoter located in the inserted vector) are shown in SEQ ID Nos.3 and 4, respectively.

Example 3

On the basis of the nucleotide sequences of SEQ ID No.1, the PCR primers shown in Table 1 were synthesized (the synthesis was entrusted to Sawady Technology Co.).

TABLE 1

| Primers | Sequences (5' to 3') |
| --- | --- |
| 1–7 | TTCACACTCGTCATTTCATTCTCGA |
| TAF1–7 | CTAATTAACTCCTCTTTACCCA |
| COMT | AATACAAGCCCCATTATCATAA |
| INT1–7 | ATATTATTAAGCCTAGGACTG |
| 1–3 | GAGTGTCAAACCACAAGCAAACAAT |
| TAF1–3 | AATTCATACGAGAAAGCTACGA |
| COPT | AGTCTATTTCTACGTTTCAGCT |
| INT1–3 | AAAACATAAGTACACATGCCAG |

PCR was carried out where the primers in Table 1 were combined as shown in Table 2 and DNAs extracted respectively from male and female spinach (strain: Ujou-1, bred by Sakata Seed Corp.) were used as templates in PCR.

TABLE 2

| Combination of primers | Male-specific DNA |
| --- | --- |
| 1–3 + COPT | absent |
| 1–3 + TAF1–7 | present |
| 1–3 + INT1–7 | absent |
| 1–7 + COMT | present |
| 1–7 + TAF1–3 | present |
| 1–7 + INT1–3 | present |
| TAF1–3 + COPT | absent |
| TAF1–3 + INT1–7 | absent |
| TAF1–3 + TAF1–7 | present |
| TAF1–7 + COMT | present |
| TAF1–7 + INT1–3 | present |
| INT1–3 + INT1–7 | absent |

DNAs were extracted by the PEX method in the same manner as in Example 1. PCR consisted of 30 cycles where each cycle was carried out at 94° C. (1 minute), 60° C. (2 minutes), and 72° C. (2 minutes) using the same Programmable Control System PC-700 (Astech) as in Example 1.

Figure 14:
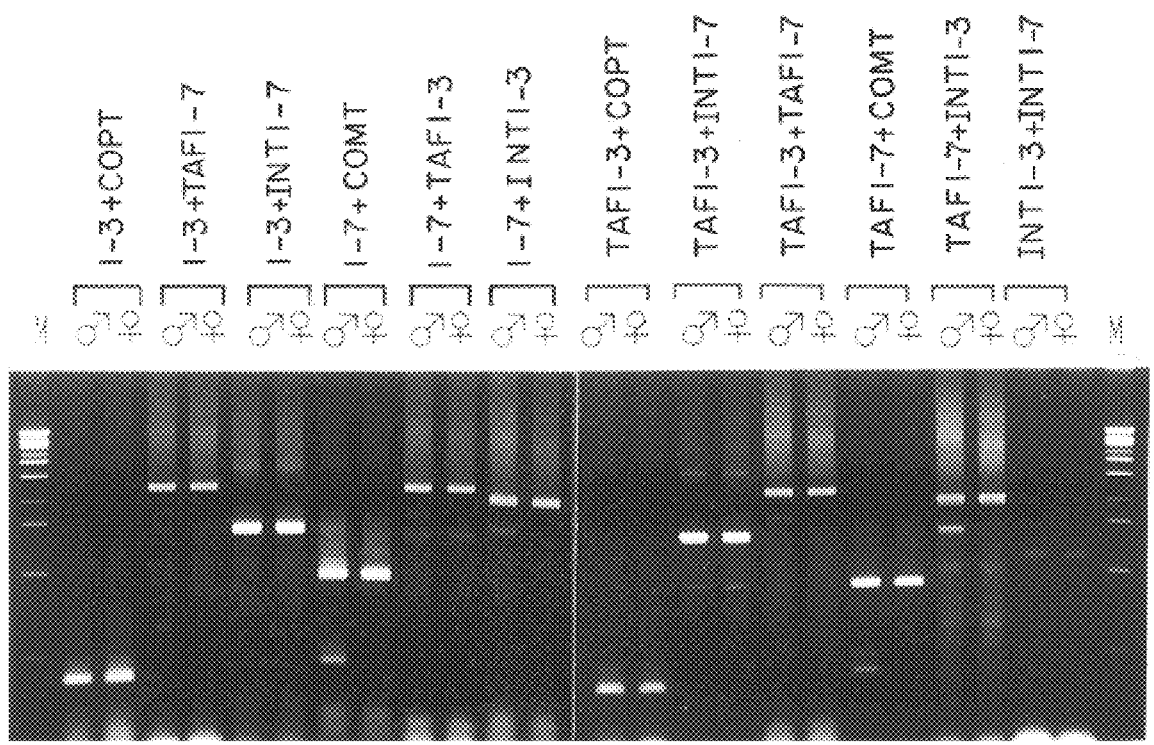
FIG. 14 is a photograph of a profile in electrophoresis of PCR amplification products with primers synthesized on the basis of the nucleotide sequence of T11 A.

To examine whether the DNA markers of estimated sizes were male-specifically amplified, the amplification products were subjected to agarose gel electrophoresis and stained in the same manner as in Example 1 The results are shown in FIG. 14 and Table 2. In FIG. 14, "M" is a molecular weight marker (Marker 6, a product of Nippon Gene K.K.). As shown in FIG. 14 and Table 2, the male-specific specific DNA maker bands could be detected in 7 combinations among the 12 primer combinations used.

Example 4

On the basis of the nucleotide sequences of SEQ ID No.2, the PCR primers shown in Table 3 were synthesized.

TABLE 3

| Primers | Sequences (5' to 3') |
| --- | --- |
| 101–7 | TACCGTTGAATCAGTTGTTGTAAGG |
| IN101–7 | GACCCTGAATGCACATTTCTGA |
| COMV | CAGACAATACAATATGAGGCTC |
| 101–3 | GTTGATCCAAGCATCGGTTAACATA |
| IN101–3 | GGTCGACAACACAGCCAATTA |
| COPV | ACCAGTTCATAAAAGAGAG |

The primers in Table 3 were combined as shown in Table 4. To examine whether the DNA markers of estimated sizes were male-specifically amplified, the amplification products were subjected to agarose gel electrophoresis and stained in the same manner as in Example 1.

TABLE 4

| Combination of primers | Male-specific DNA |
| --- | --- |
| 101–3 + COPV | absent |
| 101–3 + IN101–7 | absent |
| 101–7 + COMV | absent |
| 101–7 + IN101–3 | present |
| IN101–7 + IN101–3 | present |

Figure 15:
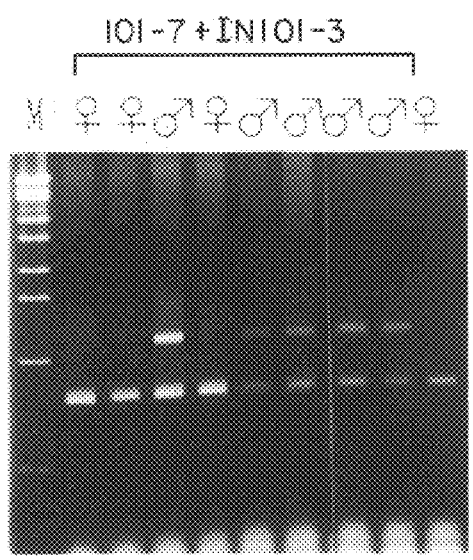
FIG. 15 is a photograph of a profile in electrophoresis of PCR amplification products with primers 101-7 and IN101-3.
Figure 16:
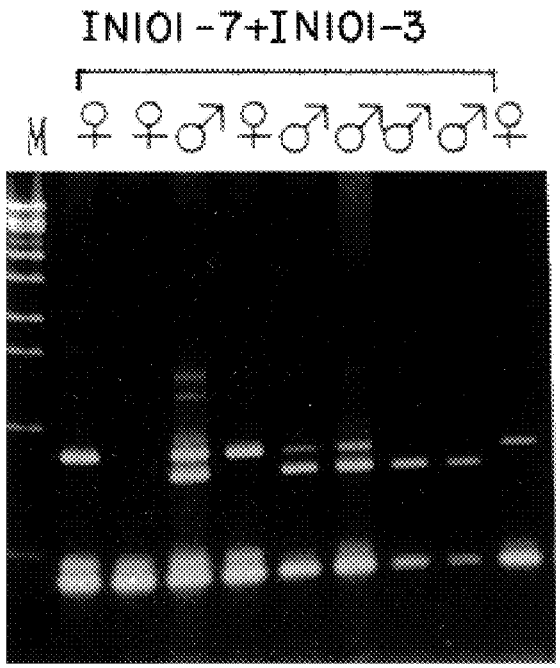
FIG. 16 is a photograph of a profile in electrophoresis of PCR amplification products with primers IN101-7 and IN101-3.

The results are shown in Table 4. The male-specific DNA maker bands could be detected in 2 combinations among the 5 primer combinations used (FIGS. 15 and 16).

Example 5

For determination of a primer combination to permit detection in the most stable manner, the respective primer combinations shown in Tables 2 and 4 were examined in PCR using DNAs extracted from different individuals, and the amplification products were examined by electrophoresis whether the object DNA makers were present or not. PCR consisted of 30 cycles where each cycle was carried out at 94° C. (15 seconds), 60° C. (30 seconds) and 72° C. (30 seconds) using Gene Amp PCR System 9600 (Perkin Elmer). The DNA was extracted in a simpler manner than in Example 3.

Figure 17:
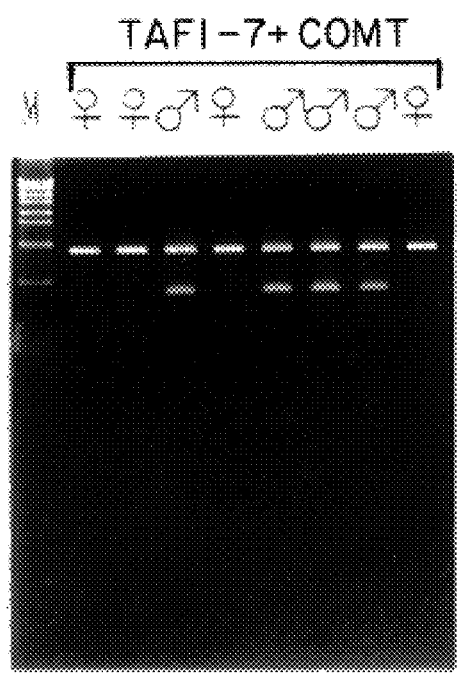
FIG. 17 is a photograph of a profile in electrophoresis of PCR amplification products with primers TAF1-7 and COMT.

Among the combinations used in this experiment, the combination TAF1-7+COMT showed the least experimental errors (FIG. 17).

What is claimed is:

1. A method for identifying the sex of a spinach plant comprising:
   (a) determining whether a sample obtained from a spinach plant contains a DNA sequence that identifies the plant as a male plant, and
   (b) identifying the sex of the plant if the plant contains the DNA sequence, or identifying the sex of the plant if the plant does not contain the DNA sequence.

2. The method of claim 1, wherein the plant is identified as a male plant if the plant contains the DNA sequence.

3. The method of claim 1, wherein the plant is identified as a female plant if the plant does not contain the DNA sequence.

4. The method of claim 1,
   wherein the DNA sequence compromises the sequence of SEQ ID:NO:1, the sequence of SEQ ID:NO:2, the sequence of SEQ ID NO:3, the sequence of SEQ ID:NO:4, the complement of the sequence of SEQ ID:NO:1, the complement of the sequence of SEQ ID:NO:2, the complement of the sequence of SEQ ID:NO:3, or the complement of the sequence of SEQ ID:NO:4.

5. The method of claim 1,
   wherein the DNA sequence is contained in the sequence of SEQ ID:NO:1, the sequence of SEQ ID:NO:2, the sequence of SEQ ID:NO:3, the sequence of SEQ ID NO:4, the complement of the sequence of SEQ ID:NO:1, the complement of the SEQ ID NO:2, the complement of the sequence of SEQ ID:NO:3, or the complement of the sequence of SEQ ID:NO:4,
   and the sequence is found in a male plant and is not found in a female plant.

6. A method for identifying the sex of a spinach plant comprising:
   (a) providing the DNA of a spinach plant,
   (b) providing first and second primers,
   wherein the first and second primers each comprise a sequence which hybridizes to the sequence of SEQ ID:NO:1, the sequence of SEQ ID:NO:2, the sequence of SEQ ID:NO:3, the sequence of SEQ ID:NO:4, the complement of the sequence of SEQ ID:NO:1, the complement of the sequence of SEQ ID:NO:2, the complement of the sequence of SEQ ID:NO:3, or the complement of the sequence of SEQ ID:NO:4,
   (c) conducting an amplification reaction using the DNA of the plant and the first and second primers,
   (d) determining whether a DNA sequence that identifies the plant as a male plant is produced during the amplification reaction, and
   (e) identifying the sex of the plant if the DNA sequence is produced, or identifying the sex of the plant if the DNA sequence is not produced.

7. The method of claim 6, wherein the plant is identified as a male plant if the DNA sequence is produced.

8. The method of claim 6, wherein the plant is identified as a female plant if the DNA sequence is not produced.

9. The method of claim 6, wherein the first primer comprises the sequence of SEQ of SEQ ID:NO:5, SEQ ID:NO:6, SEQ ID:NO:7, SEQ ID:NO:8, SEQ ID:NO:9, SEQ ID:NO:10, SEQ ID:NO:11, SEQ ID:NO:12, SEQ ID:NO:13, SEQ ID:NO:14, SEQ ID:NO:15, SEQ ID:NO:16, SEQ ID: NO:17, SEQ ID:NO:18, SEQ ID:NO:19, SEQ ID:NO:20, SEQ ID:NO:21, SEQ ID:NO:22, SEQ ID:NO:23, SEQ ID:NO:24,.

10. The method of claim 6,
wherein the first primer comprises the sequence of SEQ ID NO:9, and
the second primer comprises the sequence of SEQ ID NO:6.

11. The method of claim 6,
wherein the first primer comprises the sequence of SEQ ID NO:5, and
the second primer comprises the sequence of SEQ ID NO:7.

12. The method of claim 6,
wherein the first primer comprises the sequence of SEQ ID NO:5, and
the second primer comprises the sequence of SEQ ID NO:10.

13. The method of claim 6,
wherein the first primer comprises the sequence of SEQ ID NO:5, and
the second primer comprises the sequence of SEQ ID NO:12.

14. The method of claim 6,
wherein the first primer comprises the sequence of SEQ ID NO:10, and
the second primer comprises the sequence of SEQ ID NO:6.

15. The method of claim 6,
wherein the first primer comprises the sequence of SEQ ID NO:6, and
the second primer comprises the sequence of SEQ ID NO:7.

16. The method of claim 6,
wherein the first primer comprises the sequence of SEQ ID NO:6, and
the second primer comprises the sequence of SEQ ID NO:12.

17. The method of claim 6,
wherein the first primer comprises the sequence of SEQ ID NO:13, and
the second primer comprises the sequence of SEQ ID NO:17.

18. The method of claim 6,
wherein the first primer comprises the sequence of SEQ ID NO:14, and
the second primer comprises the sequence of SEQ ID NO:17.

19. A method for identifying the sex of a spinach plant comprising:
(a) providing the DNA of a spinach plant,
(b) providing a primer comprising the sequence of SEQ ID:NO:21, SEQ ID:NO:22, SEQ ID:NO:23, or SEQ ID:NO:24,
(c) conducting an amplification reaction using the DNA of the plant and the primer,
(d) determining whether a DNA sequence that identifies the plant as a male plant is produced during the amplification reaction, and
(e) identifying the sex of the plant if the DNA sequence is produced, or identifying the sex of the plant if the DNA sequence is not produced.

20. The method of claim 19, wherein the plant is identified as a male plant if the DNA sequence is produced.

21. The method of claim 19, wherein the plant is identified as a female plant if the DNA sequence is not produced.

22. An isolated DNA sequence comprising a sequence selected from the group consisting of the sequence of SEQ ID:NO:1, the sequence of SEQ ID:NO:2, the sequence of SEQ ID:NO:3, the sequence of SEQ ID:NO:4, the complement of the sequence of SEQ ID:NO:1, the complement of the sequence of SEQ ID:NO:2, the complement of the sequence of SEQ ID:NO:3, and the complement of the sequence of SEQ ID:NO:4.

23. An isolated DNA sequence comprising a sequence selected from the group consisting of the sequence of SEQ ID:NO:5, the sequence of SEQ ID:NO:6, the sequence of SEQ ID:NO:7, the sequence of SEQ ID:NO:8, the sequence of SEQ ID:NO:9, the sequence of SEQ ID:NO:10, the sequence of SEQ ID:NO:11, the sequence of SEQ ID:NO:12, the sequence of SEQ ID:NO:13, the sequence of SEQ ID:NO:14, the sequence of SEQ ID:NO:15, the sequence of SEQ ID:NO:16, the sequence of SEQ ID:NO:17, the sequence of SEQ ID:NO:18, the sequence of SEQ ID:NO:19, the sequence of SEQ ID:NO:20, the sequence of SEQ ID:NO:21, the sequence of SEQ ID:NO:22, the sequence of SEQ ID:NO:23, the sequence of SEQ ID:NO:24, the complement of the sequence of SEQ ID:NO:5, the complement of the sequence of SEQ ID:NO:6, the complement of the sequence of SEQ ID:NO:7, the complement of the sequence of SEQ ID:NO:8, the complement of the sequence of SEQ ID:NO:9, the complement of the sequence of SEQ ID:NO:10, the complement of the sequence of SEQ ID:NO:11, the complement of the sequence of SEQ ID:NO:12, the complement of the sequence of SEQ ID:NO:13, the complement of the sequence of SEQ ID:NO:14, the complement of the sequence of SEQ ID:NO:15, the complement of the sequence of SEQ ID:NO:16, the complement of the sequence of SEQ ID:NO:17, the complement of the sequence of SEQ ID:NO:18, the complement of the sequence of SEQ ID:NO:19, the complement of the sequence of SEQ ID:NO:20, the complement of the sequence of SEQ ID:NO:21, the complement of the sequence of SEQ ID:NO:22, the complement of the sequence of SEQ ID:NO:23, and the complement of the sequence of SEQ ID:NO:24.

24. An isolated DNA sequence consisting of a sequence selected from the group consisting of the sequence of SEQ ID:NO:5, the sequence of SEQ ID:NO:6, the sequence of SEQ ID:NO:7, the sequence of SEQ ID:NO:8, the sequence of SEQ ID:NO:9, the sequence of SEQ ID:NO:10, the sequence of SEQ ID:NO:11, the sequence of SEQ ID:NO:12, the sequence of SEQ ID:NO:13, the sequence of SEQ ID:NO:14, the sequence of SEQ ID:NO:15, the sequence of SEQ ID:NO:16, the sequence of SEQ ID:NO:17, the sequence of SEQ ID:NO:18, the sequence of SEQ ID:NO:19, the sequence of SEQ ID:NO:20, the sequence of SEQ ID:NO:21, the sequence of SEQ ID:NO:22, the sequence of SEQ ID:NO:23, the sequence of SEQ ID:NO:24, the complement of the sequence of SEQ ID:NO:5, the complement of the sequence of SEQ ID:NO:6, the complement of the sequence of SEQ ID:NO:7, the complement of the sequence of SEQ ID:NO:8, the complement of the sequence of SEQ ID:NO:9, the complement of the sequence of SEQ ID:NO:10, the complement of the sequence of SEQ ID:NO:11, the complement of the sequence of SEQ ID:NO:12, the complement of the sequence of SEQ ID:NO:13, the complement of the sequence of SEQ ID:NO:14, the complement of the sequence of SEQ ID:NO:15, the complement of the sequence of SEQ ID:NO:16, the complement of the sequence of SEQ ID:NO:17, the complement of the sequence of SEQ ID:NO:18, the complement of the sequence of SEQ ID:NO:19, the complement of the sequence of SEQ ID:NO:20, the complement of the sequence of SEQ ID:NO:21, the complement of the sequence of SEQ ID:NO:22, the complement of the sequence of SEQ ID:NO:23, and the complement of the sequence of SEQ ID:NO:24.

* * * * *

UNITED STATES PATENT AND TRADEMARK OFFICE
CERTIFICATE OF CORRECTION

PATENT NO. : 5,910,412

DATED : June 8, 1999

INVENTOR(S): Toyokazu AKAMATSU, et al.

It is certified that an error appears in the above-identified patent and that said Letters Patent is hereby corrected as shown below:

Please replace Figure 9 with new Figure 9 attached.

Please replace Figures 12 and 13 with new Figures 12 and 13 attached.

Signed and Sealed this

Fourteenth Day of November, 2000

Attest:

Q. TODD DICKINSON

Attesting Officer

Director of Patents and Trademarks

T11A (T7 SIDE)

```
TTCCCCGCGA CTTCACACTC GTCATTTCAT TCTCGACCCT AATTAACTCC TCTTTACCCA   60
  OPT11        1-7 primer                    TAF1-7 primer
ATTAGAAATC AATGCTGAAA AAAGTCTATT TCGAAATCTA GCCCTTTGTT TTTAGTCATG  120

TTTTTTGTCT AATCTATGTA AAAATCTAGG TTAAACATAA TATATTTCCA ATTTGTTATG  180

GAAGGAAGAC TTATATATAT GCTTATATTG TGGGGATTCT ATGAGAATCA GTTCAACCAC  240

TACATCAGAT TGATTTGTTT ATGCATTTTG TCCAAATATC ATGTTATCAT ATACTTGTAT  300

TTAATTTCTC GAACATATTA TTAAGCCTAG GACTGTTATG ATAATGGGGC TTGTATTTCT  360
                          INT1-7 primer         COMT primer
TATGGGAGGG GAAATGCATC ATTGATTTCC AATGAAATGG GAATTAGTT              409
```

FIG. 8

T11A (T3 SIDE)

```
TTCCCCGCGA TAGAGTGTCA AACCACAAGC AAACAATGAA TTCAAATTAC CAATAAAAAA   60
  OPT11              1-3 primer
TTCATACGAG AAAGCTACGA GATCACAACC AAGAAGTCTG CAATTCTGCA AAAAAAAACG  120
 TAF1-3 primer
TGAACATACA CTACTTTTAA AGAGATTAAC TGGATGAGAA CACTTACATA AGTAATATCC  180

CTACAGCCCC CTTCATTCTA CAGCAGAAAT CTTTGCATCA CAAGCTATAA TCCCAAAAAT  240

ACACATACCA GATATGACCA ACACTAACAA AAAAATAGAA AACATAAGTA CACATGCCAG  300
                                                 INT1-3 primer
GAAGCTGAAA CGTAGAAATA GACTCACAAA                                   330
   COPT primer
```

FIG. 9

V20C (T7 SIDE)

```
CAGCATGGTC AACTTTGGAA CAAAACACAC GAAGTCAACA TTTCAGGTTA TAAAGGAATT    60
  DPV20            12-7 primer
CCTAAGGCAC ACAGGCCAAA TTGCACAAAA GCACCATCAA TGCATGTGCA GCAGCTGCAT   120

CAAAGANTAG CAAATNATGC AGACGGTACC AGTAGTTCAT ATGCAGCAGC TGCACCAAGC   180

AGTCAAGAAC GTCAATGCAC CAGCAGCAGC AGNACAANGC ATCANGTATA AAGCANTANC   240

TTCATAAGAA CTGCATAACA TACACTAGAN CAAACANCAA GCCTGTATAA NGGGCTATAG   300

TCAGCAGGCT CCCAGCAAGC CTGATCAGNA GGTTNCTNGC AAGNCTGCTT TTGAGTAAGG   360

TTCAA                                                              365
```

*FIG. 12*

V20C (T3 SIDE)

```
CAGCATGGTC TTGCATTGTG CATGATAACG GAGTAATACA GTTATTGACT TGCCTCTCAT    60
  DPV20            12-3 primer
TGACATCATA TATAGTATAA ATGGAAAACA TTGACATCAA CAAACCCCAA ACCTTAGTAC   120

TGGTTGTATA TAAACTGGTG TTGTTGTTGT CCTTGTATCA CANCTCGGCT CTATAGGTGT   180

CGAACCTGGG CCTAGACCCT CGGAATGGAA GGTCTATTAA GAAAAGTTAG ATGCCTAGTT   240

CATGCATTAG TAAATCTACT TCTGCATTCA GCATTTGANT TATACTGGCC ATTGTGCATT   300

CGGTCAACCG GCCAATGGCT TTACCAACCC ANGCCCCTGC CTGT                   344
```

*FIG. 13*

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 1659 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: SPINACH (xi) SEQUENCE DESCRIPTION: SEQ ID NO:1:

```
TTCCCCGCGA CTTCACACTC GTCATTTCAT TCTCGACCCT AATTAACTCC TCTTTACCCA        60

ATTAGAAATC AATGCTGAAA AAGTCTATT TCGAAATCTA GCCCTTTGTT TTTAGTCATG        120

TTTTTTGTCT AATCTATGTA AAAATCTAGG TTAAACATAA TATATTTCCA ATTTGTTATG       180

GAAGGAAGAC TTATATATAT GCTTATATTG TGGGGATTCT ATGAGAATCA GTTCAACCAC       240

TACATCAGAT TGATTTGTTT ATGCATTTTG TCCAAATATC ATGTTATCAT ATACTTGTAT       300

TTAATTTCTC GAACATATTA TTAAGCCTAG GACTGTTATG ATAATGGGGC TTGTATTTCT       360

TATGGGAGGG GAAATGCATC ATTGATTTCC AATGAAATGG GAATTAGTTA TTATAATCAC       420

GAGTACATGA TTATAATAAA TGTGAAGAAC AGGGCAATAT GCTAGAAATT GCCCCTTACA       480

AAGGGATAAT GCGGATGTTA GAGAACAAGT TGTTGTAGTG GTTAATATGC TAGTTTGAAG       540

GGATATAATG GTGATGATAG ACTGGTAGAA ATGTCCATGG TGGTGTTTAG GTGATGATAT       600

GATTTACTTT GGATGTGGTC ATGCTGGTAT TTAGAAAAAA CATGGGGGTG GTACAAAATA       660

CAGAGGTGCT ACCGTGCTTG TTGGACCTAG TGGCTATGAT ATGCTAACAG AGTCAATAGT       720

TTTGACTAGG AATAAATATA CACATAATAT TTTTGACGGG CTGATGTTTC CTTCTGGCGT       780

TGATTTTCAC GATTTACTAA TGACAGATGG ATAAGATGTT TTCATTTTAG ATAAAGAATA       840

GACAAGTTAT TTATCATTTG AATCCTTGCA ACAACGATTT TTTGACAAAA TTTGCATAGC       900

TCAACCTTTA TGATTACTGA TGAGGCATGA TGAGTTTTTT CATAATCAAC TATTCTACTT       960

TGAGTAGGTT GCTAATATCG TATGTTTTCC ATCTTTAACT TGTGAAACTT AGCCAACAGG      1020

TGAAAACATA TTGTTACGCC TCAGATATAC ATGACACATG GATTGGTAGT ATGGCAGGAT      1080

TGTGAACCTC TATAATGTTA CTTTCTGGAG ACTGCAGAAT ACTTGAAAAC ACTTCAGCCT      1140

TCAAGTACTT TATTTTTTCT TCTGTCGACT CACACATGCT TGTTCTTCTT GGCAGTGTTA      1200

AGAGTTCCTC TAATTTATAT TATTATGCTG TTCATCTTTA TGTGGTTAGG GGGTCATTAG      1260

AAGTGGCAAT AGGTTGCTAC GCAAGATTGT TTGCTTGATT GATCTGGAAA TTTTATTTGC      1320

TGTTATTCTT TTGTGAGTCT ATTTCTACGT TTCAGCTTCC TGGCATGTGT ACTTATGTTT      1380

TCTATTTTTT TGTTAGTGTT GGTCATATCT GGTATGTGTA TTTTTGGGAT TATAGCTTGT      1440

GATGCAAAGA TTTCTGCTGT AGAATGAAGG GGGCTGTAGG GATATTACTT ATGTAAGTGT      1500

TCTCATCCAG TTAATCTCTT TAAAAGTAGT GTATGTTCAC GTTTTTTTTT GCAGAATTGC      1560

AGACTTCTTG GTTGTGATCT CGTAGCTTTC TCGTATGAAT TTTTTATTGG TAATTTGAAT      1620

TCATTGTTTG CTTGTGGTTT GACACTCTAT CGCGGGGAA                             1659
```

(2) INFORMATION FOR SEQ ID NO:2:

(i) SEQUENCE CHARACTERISTICS:
        (A) LENGTH: 1347 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SPINACH (xi) SEQUENCE DESCRIPTION: SEQ ID NO:2:

```
CAGCATGGTC CCTACCGTTG AATCAGTTGT TGTAAGGTAA AGCCTGAGTG GAGAACCCGA      60

TATTGTTGGC TTTAACACTG GTGGATTTGA AAATTAGTCC TTGATGGTGT CAAATGCGTA     120

TTGGCAGCCT TCGTCCCATA CCTTGGGCTC ACTCTTGTGG AGTTTTTGGA ACACTTTCTC     180

ACAAATCATG GTGAGTTTTA AAATGTACCT GTTGATGTAT TGTAACTTGC CAAGGAACTC     240

CCAAATTTCG TTCTCATTTG CCGGCGATTT CATGTCTAGA CTGGCCTTGT TTTTTGAAGG     300

ATCAGCCTCG ATGCCCTGAG AACTGATGAC ATACCCGAGT AACTTGCCTG ACGTGACCCT     360

GAATGCACAT TTCTGAGGAT TGAGCCTCAT ATTGTATTGT CTGAGCTTGT AGAAGAATTT     420

TCGAAGTACT GTTGTATGCT CATGTCGCTC TTTGGATTTG ACAATCATGT CGTCGACATA     480

TACCTCAAGT TCTCTGTGAA TCATGTCGCT CATGATGGTT GTGGCTATTA TTTAATAGGT     540

AGCCACCGTG TTCTTCGGTC CAAACGGCAT AACAGTGTAG CGGGTTTAGG GTTTCATGTC     600

TAGAATGGCC TTGTTTTTTG AATTGAGGAT CAGGCTCGAT GCCCCGAAAA CTGATGACAT     660

ACCCGAGTAA CATGCCTGAT GTCACCCCGA ATGCACATTT CTGAGGATAG AGCCTCATAT     720

TGTATTGTCT GAGCTTGTAG AAGAATTTTC GAAGTACTGT TGTATGCTCA TGTCGCTCTT     780

TGGATTTGAC AATTATGTCG TCGACATATT CCTCAATTTC TCTGTTAATC ATGTCGCTTA     840

TGATGGTTGT GGTTGTTATT TGATAGGTAG CCCCCGTGTT CTTCAGTCCA AACGGCATAA     900

CTGTTTAGCA ATATGTACCC CACTTAGTGA TGAAGGTTGT CTTCTCCATG TCGTCCTCTG     960

CTATGGGAAT CCGATTGTAG CCTGCGTACC AGTTCATAAA AGAGAGTAAG GCATAATTGG    1020

CTGTGTTGTC GACCAGAATG TCGATGAGTG GCAGTGGAAA ATCGTCTTTA GGGCTAGTCG    1080

TGTTAAGATA TCTGTAATCG ACGCACATTT GAAATTTACC GTCCTTCTTC GGAACTGGAA    1140

CGACATTTGC AATCAATTCT GAATATTTGG ATTCTCGAAT AAACCCGACC TCTAACTGCT    1200

TGGAGACCTC TTCTTTAATT TTGAGGGAAA CACCCGGTTT CACACGACGG AGTTTTTCT     1260

TGATGGGATT TATGCCTGAA ATGAGGGGAA TTGTATGTTA ACCGATGCTT GGATCAACCC    1320

CTGGCATATC ATGATAGGAC CATGCTG                                        1347
```

(2) INFORMATION FOR SEQ ID NO:3:

(i) SEQUENCE CHARACTERISTICS:
        (A) LENGTH: 365 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SPINACH (xi) SEQUENCE DESCRIPTION: SEQ ID NO:3:

```
CAGCATGGTC AACTTTGGAA CAAAACACAC GAAGTCAACA TTTCAGGTTA TAAAGGAATT      60

CCTAAGGCAC ACAGGCCAAA TTGCACAAAA GCACCATCAA TGCATGTGCA GCAGCTGCAT     120
```

CAAAGANTAG CAAATNATGC AGACGGTACC AGTAGTTCAT ATGCAGCAGC TGCACCAAGC    180

AGTCAAGAAC GTCAATGCAC CAGCAGCAGC AGNACAANGC ATCANGTATA AAGCANTANC    240

TTCATAAGAA CTGCATAACA TACACTAGAN CAAACANCAA GCCTGTATAA NGGGCTATAG    300

TCAGCAGGCT CCCAGCAAGC CTGATCAGNA GGTTNCTNGC AAGNCTGCTT TTGAGTAAGG    360

TTCAA                                                                365

(2) INFORMATION FOR SEQ ID NO:4:

(i) SEQUENCE CHARACTERISTICS:
        (A) LENGTH: 344 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: SPINACH (xi) SEQUENCE DESCRIPTION: SEQ ID NO:4:

CAGCATGGTC TTGCATTGTG CATGATAACG GAGTAATACA GTTATTGACT TGCCTCTCAT     60

TGACATCATA TATAGTATAA ATGGAAAACA TTGACATCAA CAAACCCCAA ACCTTAGTAC    120

TGGTTGTATA TAAACTGGTG TTGTTGTTGT CCTTGTATCA CANCTCGGCT CTATAGGTGT    180

CGAACCTGGG CCTAGACCCT CGGAATGGAA GGTCTATTAA GAAAAGTTAG ATGCCTAGTT    240

CATGCATTAG TAAATCTACT TCTGCATTCA GCATTTGANT TATACTGGCC ATTGTGCATT    300

CGGTCAACCG GCCAATGGCT TTACCAACCC ANGCCCCTGC CTGT                    344

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

TTCACACTCG TCATTTCATT CTCGA                                          25

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:6:

CTAATTAACT CCTCTTTACC CA                                             22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:7:

AATACAAGCC CCATTATCAT AA                                            22

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:8:

ATATTATTAA GCCTAGGACT G                                             21

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:9:

GAGTGTCAAA CCACAAGCAA ACAAT                                         25

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:10:

AATTCATACG AGAAAGCTAC GA                                            22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

AGTCTATTTC TACGTTTCAG CT                                            22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:12:

AAAACATAAG TACACATGCC AG                                                22

(2) INFORMATION FOR SEQ ID NO:13:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:13:

TACCGTTGAA TCAGTTGTTG TAAGG                                             25

(2) INFORMATION FOR SEQ ID NO:14:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:14:

GACCCTGAAT GCACATTTCT GA                                                22

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:15:

CAGACAATAC AATATGAGGC TC                                                22

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:16:

GTTGATCCAA GCATCGGTTA ACATA                                             25

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear -continued (ii) MOLECULE TYPE: other nucleic acid
    (A) DESCRIPTION: /desc = "SYNTHETIC DNA"

(xi) SEQUENCE DESCRIPTION: SEQ ID NO:17:

GGTCGACAAC ACAGCCAATT A                                      21

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:18:

ACCAGTTCAT AAAAGAGAG                                         19

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:19:

ACTTTGGAAC AAAACACACG AAGTC                                  25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:20:

GCATTGTGCA TGATAACGGA GTAAT                                  25

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:21:

TTCCCCGCGA                                                   10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear -continued (ii) MOLECULE TYPE: other nucleic acid
    (A) DESCRIPTION: /desc = "SYNTHETIC DNA"

(xi) SEQUENCE DESCRIPTION: SEQ ID NO:22:

TCGCCCAGTC                                                        10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:23:

CTGCGCTGGA                                                        10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:24:

CAGCATGGTG                                                        10